US008894559B2

(12) United States Patent
Alomair

(10) Patent No.: US 8,894,559 B2
(45) Date of Patent: Nov. 25, 2014

(54) SPINNING DISC CENTRIFUGE ROTOR

(75) Inventor: Osamah Ali Alomair, Alfayha (KW)

(73) Assignee: Kuwait University, Safat (KW)

( * ) Notice: Subject to any disclaimer, the term of this patent is extended or adjusted under 35 U.S.C. 154(b) by 919 days.

(21) Appl. No.: 13/053,102

(22) Filed: Mar. 21, 2011

(65) Prior Publication Data
US 2012/0245013 A1 Sep. 27, 2012

(51) Int. Cl.
B04B 7/08 (2006.01)
B04B 5/04 (2006.01)
G01N 9/30 (2006.01)
G01N 13/00 (2006.01)
B01L 3/00 (2006.01)

(52) U.S. Cl.
CPC ... *B04B 5/04* (2013.01); *B04B 7/08* (2013.01); *G01N 9/30* (2013.01); *G01N 13/00* (2013.01); *B01L 3/523* (2013.01)
USPC .................. 494/10; 494/43; 494/38; 422/533

(58) Field of Classification Search
USPC ........ 494/10, 43, 85, 64, 38–41; 422/72, 548, 422/551, 533; 435/305.4; 210/781, 360.1, 210/380.1
See application file for complete search history.

(56) References Cited

U.S. PATENT DOCUMENTS

| 3,241,753 | A | * | 3/1966 | Ende | 494/43 |
| 3,241,754 | A | * | 3/1966 | Ende | 494/43 |
| 3,243,106 | A | * | 3/1966 | Atherton et al. | 494/37 |
| 3,986,534 | A | | 10/1976 | Schmidt | |
| 4,409,820 | A | * | 10/1983 | Nash | 73/61.64 |
| 4,671,102 | A | | 6/1987 | Vinegar et al. | |
| 4,740,077 | A | | 4/1988 | Goodwill | |
| 5,328,440 | A | | 7/1994 | Chen et al. | |
| 5,783,760 | A | | 7/1998 | Haines et al. | |
| 6,059,712 | A | | 5/2000 | Corlett et al. | |
| 6,544,162 | B1 | * | 4/2003 | Van Wie et al. | 494/37 |
| 7,144,361 | B2 | | 12/2006 | Aizawa et al. | |
| 7,352,179 | B2 | | 4/2008 | Chen et al. | |
| 7,727,136 | B2 | * | 6/2010 | Kim et al. | 494/10 |
| 7,803,101 | B2 | * | 9/2010 | Porto | 494/11 |
| 7,988,610 | B2 | * | 8/2011 | Oki et al. | 494/37 |
| 2012/0245013 | A1 | * | 9/2012 | Alomair | 494/10 |

FOREIGN PATENT DOCUMENTS

| CA | 1313516 C | 2/1993 |
| CN | 2259629 Y | 8/1997 |
| DE | 4033069 A1 | 4/1992 |
| JP | 2007152209 A | 6/2007 |

OTHER PUBLICATIONS

S.M. Al-Modhi and R.L. Christiansen, "The 'Spinning Disk' Approach to Capillary Pressure Measurement with a Centrifuge Experiment," Int. Symp. of the SCA, La Hague, Sep. 14-16, 1998.
Osamah A. Al-Omair and R.L. Christiansen, "Benefits of Saturation Profiles for Estimating Gas and Liquid Relative Permeabilities From Centrifuge Tests," J. Pet. Sci. Eng., 46(1-2) 2005.
Chen et al., "A Single-Shot Method for Determining Drainage and Imbibition Capillary Pressure Curves," Int. Symp. of the SCA, Trondheim, Norway, 2006.
Osamah A. Al-Omair, "New Experimental Approach for Measuring Drainage and Spontaneous Imbibition Capillary Pressure", *Energy Fuels*, Jan. 2009, 23 (1), pp. 260-271.

* cited by examiner

*Primary Examiner* — Charles Cooley
(74) *Attorney, Agent, or Firm* — Richard C Litman

(57) ABSTRACT

The spinning disc centrifuge rotor includes a sample holder formed from a cylindrical disc body and a cover plate that are made from a transparent material, such as polycarbonate. The disc-shaped body has two concentric or coaxial recesses defined therein. The first recess forms a cylindrical well or sample chamber for receiving a generally cylindrical rock sample. The second recess has a larger diameter than the first recess, and is shallower, forming a fluid collection area above the sample well, the second recess forming an annular ring extending around the top edge or rim of the sample well. An O-ring snugly within the outer wall of the second recess and forms a seal between the cover plate and the floor of the second recess, preventing fluid leakage. A rotor shaft extends from the bottom face of the cylindrical disc.

12 Claims, 4 Drawing Sheets

SPINNING DISC CENTRIFUGE ROTOR

BACKGROUND OF THE INVENTION

1. Field of the Invention

The present invention relates to devices for capillary pressure and relative permeability testing of rock samples to evaluate petroleum deposits, and particularly to a spinning disc centrifuge rotor having a novel sample holder for performing spinning disc-type centrifugation of a cylindrical core sample.

2. Description of the Related Art

A centrifuge is a piece of laboratory equipment, generally driven by an electric motor (although some older models were spun by hand), which puts an object in rotation around a fixed axis, applying a force perpendicular to the axis. The centrifuge works through the sedimentation principle, where the centripetal acceleration causes more dense substances to separate out along the radial direction (i.e., toward the bottom of a collection tube). By the same principle, lighter objects will tend to move to the top of the collection tube (i.e., toward the center of rotation).

The centrifugal force acts as an effective gravitational force, and increasing this effective gravitational force will more rapidly and completely cause the precipitate (often referred to as the "pellet") to gather on the bottom of the tube. The remaining solution is called the "supernate" or "supernatant". The supernatant liquid is then typically either quickly decanted from the tube (without disturbing the precipitate), or withdrawn with a Pasteur pipette. The rate of centrifugation is specified by the acceleration applied to the sample, typically measured in revolutions per minute (RPM) or as a multiple of gravitational acceleration at the Earth's surface, g. The particles' settling velocity in centrifugation is a function of their size and shape, centrifugal acceleration, the volume fraction of solids present, the density difference between the particle and the liquid, and the viscosity.

Porous solids containing liquids provide unique challenges in centrifugation. For example, performing a capillary pressure measurement during centrifugation of a solid rock sample that contains liquid petroleum products requires a substantially different centrifugation procedure than performing centrifugation on liquid solution or a mostly liquid suspension.

FIG. 2 diagrammatically illustrates an early centrifuge system 100 for studying capillary pressure and similar properties in a core sample S, which may be a core sample of rock containing petroleum products or the like. In the system 100, the core sample S is fixed at one end to a rotating arm 102, which is, in turn, fixed at its other end to a rotating axle A. As the axle A spins, as in conventional centrifugation, the liquid petroleum products within sample S migrate through the porous rock, from the inner radius $R_1$ toward the outer radius $R_2$.

This relatively simple arrangement, however, makes both direct measurements and calculated predictions extremely difficult. In order to properly calculate capillary pressure, for example, a model must be used in which the rock sample is assumed to be homogeneous, the sample S must be perfectly cylindrical, and centrifugal acceleration must be parallel to the cylindrical axis of the sample S at all times.

In order to make measurements easier, and also to provide for greater accuracy in calculations, an arrangement for centrifugation as shown in FIG. 3 is desirable. As shown, the cylindrical core sample in FIG. 3 is rotated about a central axis X, which is coaxial with the cylindrical axis of the sample itself. FIGS. 4 and 5 illustrate a simplified prior art "spinning disc" centrifuge 200 for centrifuging a cylindrical core sample about the cylindrical axis, as in FIG. 3.

In the centrifuge 200, a sample cell 206 is mounted on a plate 202. As shown in FIG. 4, the sample cell 206 has a cylindrical sample chamber 212 formed therein for receiving a cylindrical core sample. The plate 202 may be mounted on a rotating support 204, which is coupled (via a conventional coupler 208) to a driven rotating axle 210. A plurality of collection vessels 214 are in communication with the sample chamber 212 (extending radially outwardly therefrom) to collect liquids that flow from the porous rock sample under centrifugal force.

The spinning disc centrifuge 200 provides a major improvement over the system 100, allowing for the testing of large core samples, providing validity for the assumption of zero capillary pressure at an outlet face, allowing for the measurement of local saturation at any given time, and providing the possibility of estimating drainage and spontaneous capillary pressure. These, along with consideration of radial effects and the ability to estimate relative permeability using both fluid production and saturation distribution, however, are all only within the realm of possibility with the conventional spinning disc system 200. Thus far, no spinning disc centrifuge has been produced that effectively allows for such complete measurement and testing.

Further, although such an arrangement is an improvement over the simple system 100 shown in FIG. 2, the centrifuge 200 does not allow for consolidated samples. Typically, only an unconsolidated sample could be used in system 200, with a plurality of mesh screens being provided between the sample chamber 212 and the collection vessels 214. Further, performing pressure measurements remains extremely difficult in this arrangement, since the collection vessels 214 are best used solely for collection following the completed centrifugation process.

In addition to the above, it would be desirable to be able to easily study the definition of boundary condition on the end faces of a cylindrical core plug, the gravity degradation effect at low speeds, the characterization of core sample heterogeneity, and the effect of radial centrifugal field distribution inside a core sample. Particularly, a core sample holding rotor allowing for the accurate measurement of capillary pressure and relative permeability curves would be desirable.

Thus, a spinning disc centrifuge rotor solving the aforementioned problems is desired.

SUMMARY OF THE INVENTION

The spinning disc centrifuge rotor is a transparent laboratory centrifuge rotor and sample holder of the spinning disc type; i.e., adapted for centrifugation of a cylindrical core sample, such as a porous rock sample containing petroleum products, in which rotation occurs about the central cylindrical axis of the sample. The spinning disc-type rotor and sample holder, along with the transparent nature of the rotor, allow for accurate measurements of capillary pressure, relative permeability curves, and other experimental test data commonly associated with such samples.

The spinning disc centrifuge rotor includes a sample holder formed from a cylindrical disc body and a cover plate that are made from a transparent material, such as polycarbonate, preferably Lexan® (Lexan is a registered trademark of General Electric Company of Schenectady, N.Y.). The disc-shaped body has two concentric or coaxial recesses defined therein. The first recess forms a cylindrical well or sample chamber for receiving a generally cylindrical rock sample.

The second recess has a larger diameter than the first recess, and is shallower, forming a fluid collection area above the sample well, the second recess forming an annular ring extending around the top edge or rim of the sample well. An O-ring snugly within the outer wall of the second recess and forms a seal between the cover plate and the floor of the second recess, preventing fluid leakage. A rotor shaft extends from the bottom face of the cylindrical disc.

The cover plate may be secured to the cylindrical disc by sheet metal screws, or by any other conventional fastener. The rotor shaft may be bolted to the bottom face of the cylindrical disc, or attached thereto by any conventional method.

In operation, a cylindrical rock sample saturated with a liquid (which may be two fluids of different density, e.g., oil and water) is placed in the first recess, the O-ring is placed in the outer periphery of the fluid collection chamber, and the rotor shaft is mounted in the chuck of a motor or other source of rotational motion. Liquid in the rock sample exits the top face of the sample, the fluid/fluid interface rising on top of the sample, with the heavier density fluid moving towards the fluid collection chamber by centrifugal force and the lighter density fluid collecting towards the center of the spin as the rotational speed is increased. The transparent material permits movement of the fluid to be captured on video, and the geometry of the sample holder permits evaluation of the boundary condition at the outlet face of the sample, as well as accurate measurement of capillary pressure and relative permeability curves, use of a large core sample for centrifuging, testing validity of the assumption of zero capillary pressure at the outlet face of the core sample, ability to measure local saturation at any given time, the possibility of estimating drainage and spontaneous imbibition capillary pressure, consideration of the radial effect, and the ability to estimate relative permeability using both fluid production and saturation distribution.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1A:
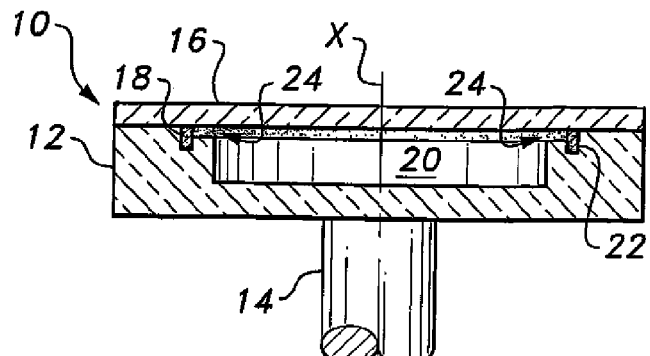
FIG. 1A is a partial side view of a spinning disc centrifuge rotor according to the present invention with the sample holder being shown in section.
Figure 1B:
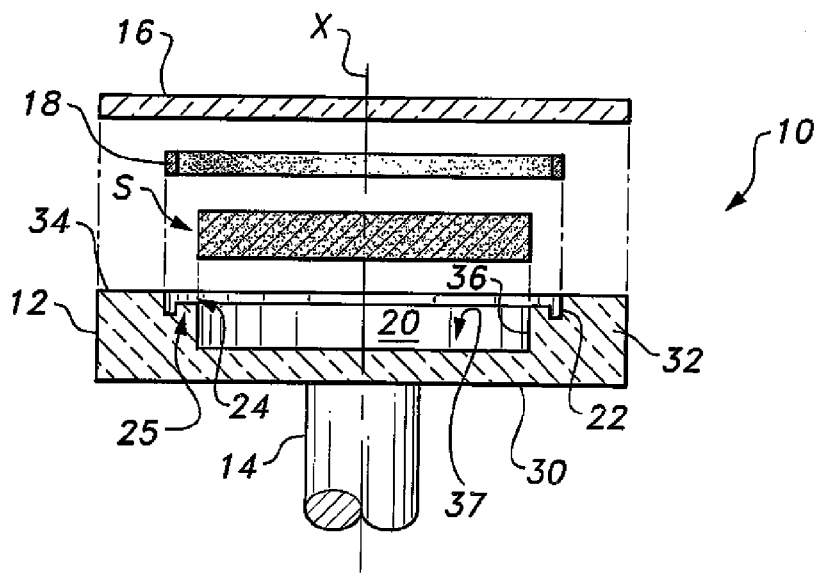
FIG. 1B is a partially exploded environmental side view of the spinning disc centrifuge rotor of FIG. 1A with the sample holder and related components being shown in section.
Figure 1C:
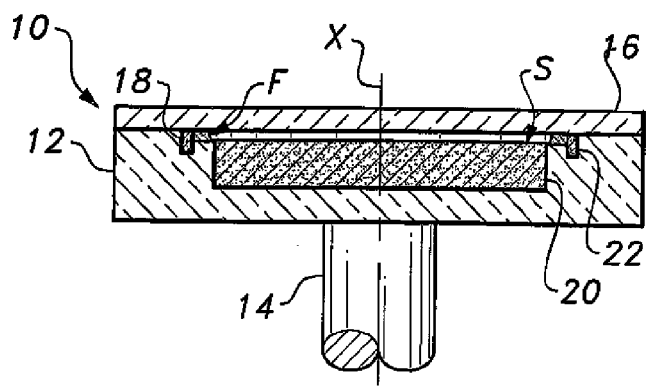
FIG. 1C is a partial environmental side view of the spinning disc centrifuge rotor of FIG. 1A, shown with the sample holder in section.
Figure 2:
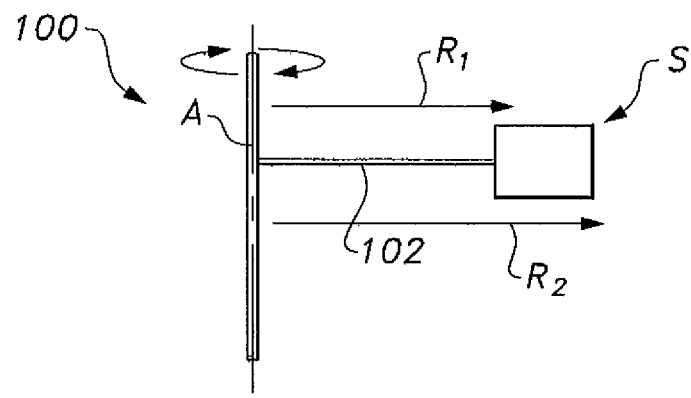
FIG. 2 is a diagrammatic side view of a typical centrifuge for measuring capillary pressure in a core sample according to the prior art.
Figure 3:
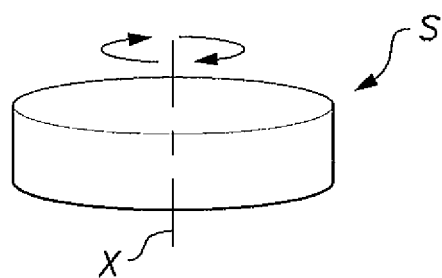
FIG. 3 is a diagrammatic side view of a spinning disc according to the prior art.
Figure 4:
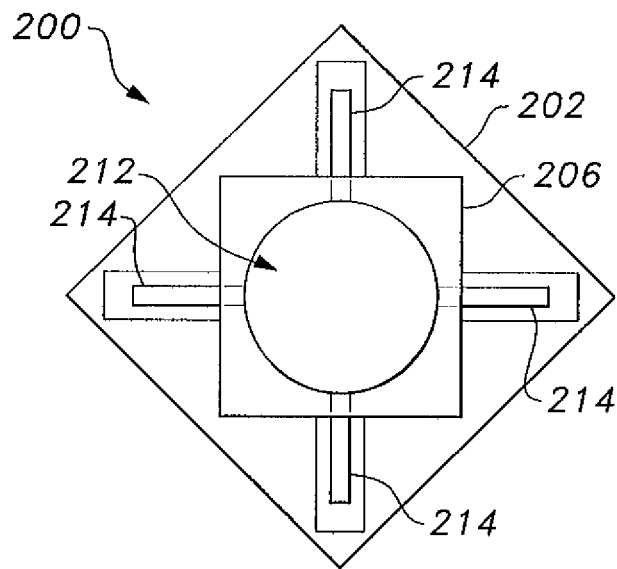
FIG. 4 is a diagrammatic top view of an exemplary spinning disc centrifuge sample holder according to the prior art.
Figure 5:
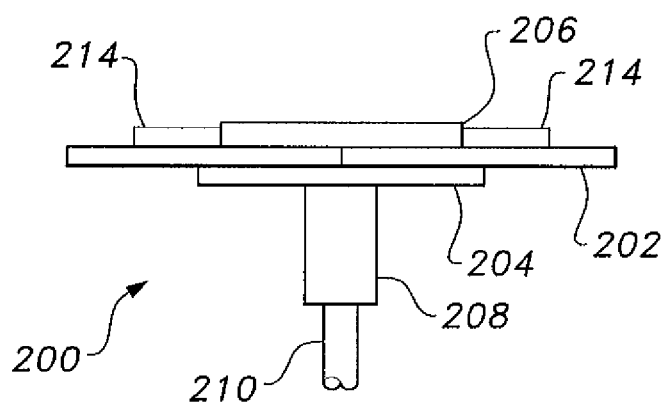
FIG. 5 is a diagrammatic side view of the spinning disc centrifuge of FIG. 4 according to the prior art.
Figure 6:
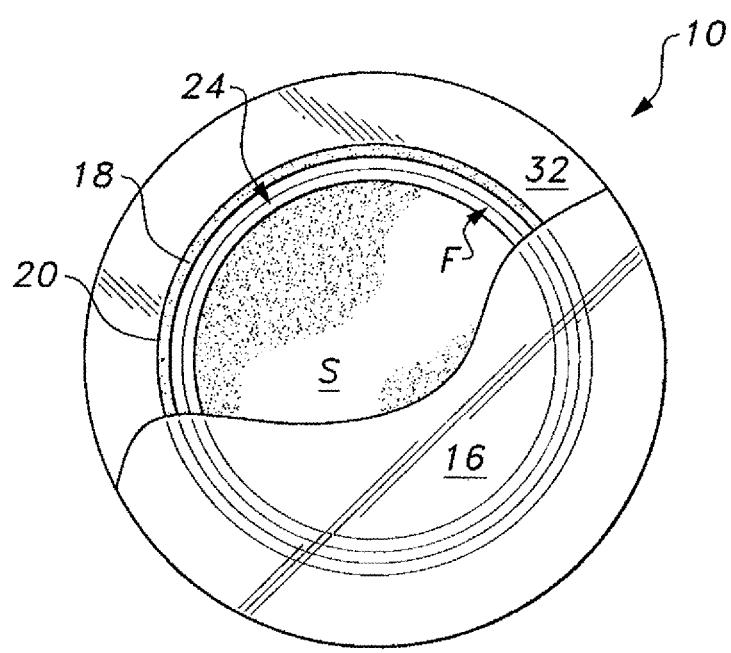
FIG. 6 is an environmental top view of the spinning disc centrifuge rotor of FIGS. 1A-1C, the cover plate being broken away to show details of the top face of the disc.

The spinning disc centrifuge rotor 10 is a transparent laboratory centrifuge rotor and sample holder of the spinning disc type; i.e., adapted for centrifugation of a cylindrical core sample, such as a porous rock sample containing petroleum products, with rotation occurring about the central cylindrical axis of the sample. In FIGS. 1B, 1C and 6, an exemplary cylindrical core sample S is illustrated. It should be understood that core sample S is shown for exemplary and illustrative purposes only. As will be described in greater detail below, the geometry and construction of the spinning disc-type rotor 10, along with the transparent nature of the rotor, allow for accurate measurements of capillary pressure, relative permeability curves, and other experimental test data commonly associated with such samples.

As shown in FIGS. 1A-1C and FIG. 6, the spinning disc centrifuge rotor 10 includes a sample holder formed from a cylindrical disc body 12 and a cylindrical cover plate 16 that are made from a transparent material, such as polycarbonate, preferably Lexan® (Lexan is a registered trademark of General Electric Company of Schenectady, N.Y., the trademark currently being owned by Sabic Innovative Plastics IP B.V. Company of the Netherlands). Alternatively, the sample holder may be made from Plexiglas® (Plexiglas is a registered trademark of Rohm & Haas Company of Philadelphia, the trademark currently being owned by Arkema France Corporation of Colombes, France), which is made from polymethyl methacrylate, another transparent plastic. The disc-shaped body 12 has a bottom face 30, a top face 34, a solid body 32 between the faces 30, 34, and two concentric or coaxial recesses 20, 24 defined therein. Recesses 20, 24 each extend from the top face 34 into the body 12, to respective predetermined depths, and the recesses 20, 24 are coaxial about an axis of rotation X. The first recess 20 forms at a first depth a comparatively deep cylindrical well or sample chamber defined by its peripheral wall 36 and planar bottom 37 for receiving a generally cylindrical core sample S. Exemplary dimensions for the rock or core sample S may be up to four inches in diameter by 0.5 inches thick.

The second recess 24 has a larger diameter than the first recess 20, and is shallower, that is, recess 24 extends to a second depth, forming a fluid collection area or fluid collection chamber for collecting fluid F above the sample well 20, the second recess 24 forming an annular ring having a planar floor 25 extending around the top edge or rim of the sample well 20. An O-ring 18 fits snugly within the outer wall of the second recess 24 and forms a seal between the cover plate 16 and the floor of the second recess 24, preventing fluid leakage. A groove 22 may be formed in the disc body 12 at the outer periphery of the second recess 24 to form a seat for the O-ring 18. The cover plate 16 is circular and covers the top face 34 of the disc body 12. The cover plate 12 may be secured to the disc body 12 by any suitable fastening means, e.g., sheet metal screws.

A rotor shaft 14 extends from the bottom face 30 of the cylindrical disc 12. The shaft 14 defines the axis of rotation X, and may be attached to the center of the bottom face 30 of the disc body 12 in any suitable manner, e.g., by bolts. The rotor shaft 14 is adapted for attachment to any device that provides a selectively actuated source of rotation, e.g., the chuck of a motor. Exemplary motive forces for centrifuges are shown in U.S. Pat. Nos. 7,422,554 and 7,352,179, each of which is hereby incorporated by reference in its entirety.

In operation, a cylindrical rock sample saturated with a liquid (which may be two fluids of different density, e.g., oil and water) is placed in the first recess, the O-ring is placed in the outer periphery of the fluid collection chamber, and the rotor shaft is mounted in the chuck of a motor or other source of rotational motion. Liquid in the rock sample exits the top face of the sample, the fluid/fluid interface rising on top of the sample, with the heavier density fluid moving towards the fluid collection chamber by centrifugal force and the lighter density fluid collecting towards the center of the spin as the rotational speed is increased. The transparent material permits movement of the fluid to be captured on video, and the geometry of the sample holder permits evaluation of the boundary condition at the outlet face of the sample, as well as accurate measurement of capillary pressure and relative permeability curves, use of a large core sample for centrifuging, testing validity of the assumption of zero capillary pressure at the outlet face of the core sample, ability to measure local saturation at any given time, the possibility of estimating drainage and spontaneous imbibition capillary pressure, consideration of the radial effect, and the ability to estimate relative permeability using both fluid production and saturation distribution.

It is to be understood that the present invention is not limited to the embodiment described above, but encompasses any and all embodiments within the scope of the following claims.

I claim:

1. A spinning disc centrifuge rotor, comprising:
   a sample holder having:
   a cylindrical disc body having an axis and an axial length extending from a top face to a bottom face, and first and second coaxial cylindrical recesses extending through the top face and into the body;
   wherein the first recess extending deep into the body at a first depth from the top face and having a first diameter, the first recess defining a sample well having an upper rim, a planar floor, and a wall extending normal between the upper rim and planar floor, and adapted for receiving a cylindrical core sample;
   wherein the second recess extending into the body at a second depth from the top face, the second depth being less than the first depth of the first recess, the second recess having a second diameter greater than the first diameter of the first recess, and forming an annular ring extending outward from the upper rim of the first recess, and an outer periphery thereabout, the annular ring defining a planar floor between the upper rim and the outer periphery; and
   a circular cover plate attachable to and covering the top face of the cylindrical disc body;
   wherein the second recess defining a fluid collection chamber between the cover plate, and the floor and the outer periphery of the second recess; and
   a rotor shaft extending from the bottom face of the cylindrical disc body, the shaft defining an axis of rotation extending coaxially through the cylindrical disc body and concentrically through the circular cover plate;
   whereby, when the shaft is rotated, fluids in the core sample exit a face of the core sample adjacent to the cover plate, and denser portions of the fluids are driven by centrifugal force towards the outer periphery of the fluid collection chamber.

2. The spinning disc centrifuge rotor as recited in claim 1, further comprising an O-ring disposed between said cover and the floor of the annular ring, fitting snugly against the outer periphery of the fluid collection chamber to form a fluid-tight seal.

3. The spinning disc centrifuge rotor as recited in claim 2, wherein said cylindrical disc body has an annular groove defined therein at the outer periphery of the fluid collection chamber, forming a seat for said O-ring.

4. The spinning disc centrifuge rotor as recited in claim 1, wherein said cylindrical disc body and said cover plate are formed from a transparent material.

5. The spinning disc centrifuge rotor as recited in claim 1, wherein said cylindrical disc body and said cover plate are formed from polycarbonate.

6. The spinning disc centrifuge rotor as recited in claim 1, wherein said cylindrical disc body and said cover plate are formed from polymethyl methacrylate.

7. A sample holder for a spinning disc centrifuge, comprising:
   a cylindrical disc body having an axis and an axial length extending from a top face to a bottom face, and first and second coaxial cylindrical recesses extending through the top face and into the body;
   wherein the first recess extending into the body at a first depth from the top face and having a first diameter, the first recess defining a sample well having an upper rim, a planar floor, and a wall extending normal between the upper rim and planar floor, and adapted for receiving a cylindrical core sample;
   wherein the second recess extending into the body at a second depth from the top face, the second depth being less than the first depth of the first recess, the second recess having a second diameter greater than the first diameter of the first recess, and forming an annular ring extending outward from the upper rim of the first recess, and an outer periphery thereabout, the annular ring defining a planar floor between the upper rim and the outer periphery; and
   a circular cover plate attachable to and covering the top face of the cylindrical disc body;
   wherein the second recess defining a fluid collection chamber between the cover plate, and the floor and the outer periphery of the second recess.

8. The sample holder according to claim 7, further comprising an O-ring disposed between said cover and the floor of the annular ring, fitting snugly against the outer periphery of the fluid collection chamber to form a fluid-tight seal.

9. The sample holder according to claim 8, wherein said cylindrical disc body has an annular groove defined therein at the outer periphery of the fluid collection chamber, forming a seat for said O-ring.

10. The sample holder according to claim 7, wherein said cylindrical disc body and said cover plate are formed from a transparent material.

11. The sample holder according to claim 7, wherein said cylindrical disc body and said cover plate are formed from polycarbonate.

12. The sample holder according to claim 7, wherein said cylindrical disc body and said cover plate are formed from polymethyl methacrylate.

* * * * *